United States Patent [19]

Imazio

[11] Patent Number: Plant 7,536

[45] Date of Patent: May 28, 1991

[54] HEATH PLANT NAMED ROSEMARIE

[75] Inventor: Bruno L. Imazio, Watsonville, Calif.

[73] Assignee: Bay City Flower Co., Half Moon Bay, Calif.

[21] Appl. No.: 447,261

[22] Filed: Dec. 7, 1989

[51] Int. Cl.[5] ..... A01H 5/00

[52] U.S. Cl. ..... Plt./54

[58] Field of Search ..... Plt./54

*Primary Examiner*—Howard J. Locker

*Attorney, Agent, or Firm*—James R. Cypher

[57] ABSTRACT

The present invention relates to a new and distinct variety of heath named 'Rosemarie', a seedling of unknown pollen parent growing in a field of *Erica persolute* 'Sunset', the variety believed to be the seed parent, which is principally distinguished from its parents and other known related varieties by its light, orchid pink colored blooms, early bloom time of December through February, its slower growth rate, its shorter height, and its natural abundant branching.

1 Drawing Sheet

BACKGROUND OF THE INVENTION

This invention relates to a new and distinct plant variety of the Ericaceae family which has been named *Erica persoluta* 'Rosemarie' by the assignee of the invention. This new heath variety was discovered by the inventor as a seedling of unknown pollen parentage growing in a cultivated field of *Erica persoluta* and *Erica persoluta 'Sunset', (U.S. Plant Pat. No.* 5,336), the cut-flower variety believed to be the seed parent. It was noticed because of its light, orchid pink colored blooms; and the following characteristics making it desirable for pot plant culture: slower growth rate, shorter height by at least one foot compared to the field, cut flower heath varieties, natural abundant branching and compact dense appearance. The new variety resembles its seed parent *Erica persoluta* 'Sunset' in its blooming habit from December through February.

The new variety is desirable for potted plant culture because of its slower growth rate and natural branching with little or no prunning which results in a shorter plant with a full, dense appearance. The closest variety of heath, cultivated as a pot plant of which I am aware, is *Erica persoluta*, and it requires numerous pruning to achieve abundant branching and the desired full, dense appearance.

The distinguishing charcteristics which are outstanding in my new variety and which distinguish it from *Erica persoluta* are:

1. early bloom time of December through February,
2. light, orchid pink colored blooms,
3. slower growth rate and shorter height
4. natural abundant branching with minimal pruning, and
5. compact, dense appearance.

Since the inventor's discovery of the new plant, the assignee, under the supervision of the inventor has reproduced it through successive generations by means of cuttings and has found that its natural dense and compact appearance and light, orchid pink colored blooms remain true from generation to generation and appear to be firmly fixed.

BRIEF DESCRIPTION OF THE DRAWING

The accompanying drawing is a color photograph of a potted plant of the new variety illustrating the overall appearance and form of the plant, abundant branching, short height dense compact appearance and light, orchid pink blooms.

DETAILED DESCRIPTION OF THE DRAWING

The following is a detailed description of the new variety with color designations according to the R.H.S. colour chart published by The Royal Horticultural Society of London, England. The following description is based on observations of well fertilized plants of 12 to 14 months of age from initial propagation which were grown outside under saran in a commercial nursery in Half Moon Bay, Calif., where tempertures average from 55 to 65 degrees F. during the summer months, and 45 to 55 degrees F. during the winter months.

Color designation and other values stated may deviate slightly from the stated values from flowering to flowering, but the deviations will be within the range expected from varying environmental, seasonal, and cultural conditions.

THE PLANT

Origin: Seedling.

Parentage:

*Seed parent.*—*Erica persoluta* 'Sunset'.

*Pollen parent.*—Unknown.

Classification:

*Botanic.*—*Erica persoluta Rosemarie'.*

*Commercial.*—'Rosemarie'.

Form: Perennial.

Shape: Generally upright, stems spreading to proudce fullness of plant.

Branching: Naturally abundant with minimal or no pruning.

Growth: Slow growth rate resulting in reduced height of plant.

Rooting Time: Three Weeks.

Foliage: Abundant, with tiny needle-like leaves over entire plant.

*Size of leaf.*—Mean ⅛ long and less than 1/16" "wide".

*Shape of leaf.*—Acerose like.

*Character.*—Sulcate.

*Color.*—R.H.S. 144A.

*Texture.13* Smooth.

*Hardiness.*—Can tolerate a temperature range of 20 to 120 degrees Fahrenheit.

*Disease resistance.*—Considerable resistance to fungus type diseases. Common diseases include phythium and phytopthora.

*Seed production.*—Sparce; comercially produced asexually by cuttings.

*Effects of weather.*—Can tolerate freezing temperatures for one week. Over 90 degree F. temperatures stress the plant.

In general, the foliage is too tiny to determine further characteristics by plant observation.

THE BUD

Size:

*Length.*—1/16".

*Diameter.*—1/16" and less.

Rate of opening: Rapid, progessive and continouous beginning at the base of stem and progressing to the tip of the stem.

Petals: Corolline flowers in which the sepals are relatively insignificant.

Color: R.H.S. 70D in early, beginning stage to 70C in the late stage before flowering.

INFLORESCENCE

Blooming habit: Annually, beginning in December and continuing through February.

Size of bloom: ⅛ by 1/16".

Borne: Compound raceme and has clusters with as many as seven terminal buds.

Shape: Urecolate.

Appearance: Satiny.

Color: R.H.S. 66D in overall appearance of the plant.

Flower stem:

*Length.*≤Mean ¼" to 2".

*Color.*—R.H.S. 177D.

*Strength.*—Woody and supple.

Discoloration: Fades slightly.

Effects of weather: Prolonged exposure to hot or wet weather is detrimental to plant appearance. Extended periods of hot dry sunshine will accelerate blooming and cause blooms to fade and decline more quickly, shortening its lasting quality. Extended wet weather will cause more mature blooms in the clusters to turn brown.

Persistence: Blooms persists long after the stem ceases to draw water.

Fragrance: Mild.

Lasting quality:

*On plant.*—2 months.

As a cut flower.—two weeks.

The outstanding characteristics of this new plant resides in its slow growth rate and abundant branching giving it a full, dense appearance making it desirable as a potted plant; its light, orchid pink colored blooms and its early blooming in December through February for the Valentines Day market, whereas *Erica persoluta* does not begin to bloom until March.

TABLE OF COMPARISON

| PLANT | NEW CULTIVAR | ERICA PERSOLUTA |
|---|---|---|
| Form | Short Dense appearing compact woody shrub | woody shrub |
| Shape | Upright, stems spreading to produce fullness of plant | Upright, stems spreading to produce fullness of plant |
| Branching | Generous, minimal or no pruning necessary | several pruning necessary to encourage branching and fullness |
| Growth | Naturally upright bat short and branching with woody, flexible strength | upright with woody flexible strength |
| Height | a 4" pot will be 8" to 9" high in 18 months growing time with little or no pruning | a 4" pot will be 10" to 12" high in 18 months growing time with numerous prunings |
| Blooming season | Annual. Dec. thru Feb. | Annual. early March thru late Mar. |
| Foliage | | |
| Color | R.H.S. 144.- | R.H.S. 143A with 59A streaking thru the leaves |
| Size | ⅛" | Same |
| Shape | Acerose like | Same |
| Quantity | Abundant | Same |
| Bloom | | |
| Size | ⅛" × 1/16" | 3/16" × 1/16" |
| Borne' | In clusters with terminal flowers | Same |
| Shape | Urceolate | Ovoid |
| Color | R.H.S. 66D | R.H.S. 70A to 70B |
| Discoloration | Fades slightly | Does not fade |

I claim:

1. A new and distinct hybrid plant variety of the Ericaceae family substantially as herein show and described.

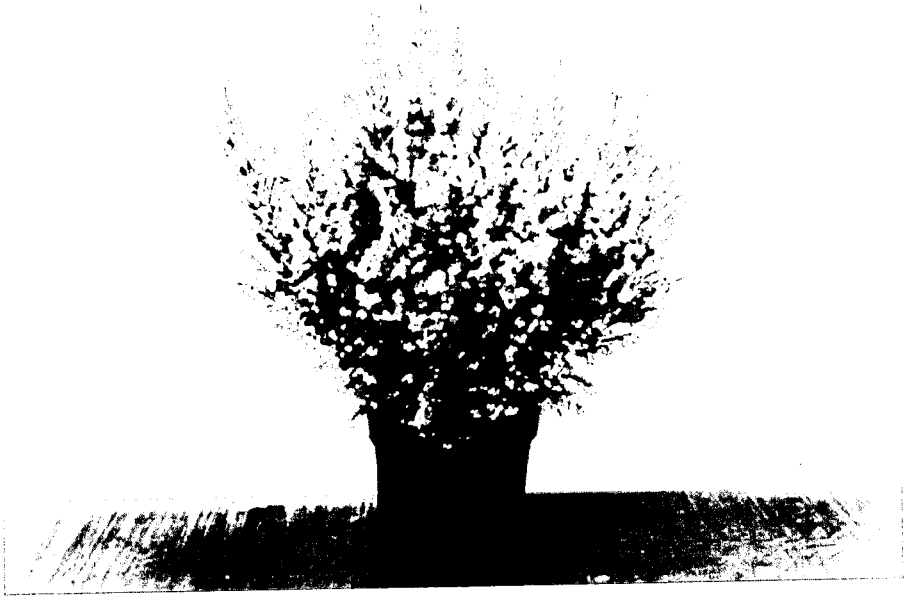

* * * * *